US00PP10228P

United States Patent [19]

Jepsen

[11] Patent Number: Plant 10,228

[45] Date of Patent: Feb. 3, 1998

[54] KALANCHOE PLANT NAMED 'JULIANA'

[75] Inventor: Knud Jepsen, Hinnerup, Denmark

[73] Assignee: Knud Jepsen A/S, Hinnerup, Denmark

[21] Appl. No.: 709,743

[22] Filed: Sep. 9, 1996

[51] Int. Cl.[6] ..... A01H 5/00

[52] U.S. Cl. ..... Plt./87.15

[58] Field of Search ..... Plt./87.15

[56] References Cited

U.S. PATENT DOCUMENTS

P.P. 9,354 10/1995 Hope ..... Plt./87.15

P.P. 9,427 1/1996 Jepsen ..... Plt./87.15

P.P. 9,428 1/1996 Jepsen ..... Plt./87.15

*Primary Examiner*—James R. Feyrer

*Assistant Examiner*—Kent L. Bell

*Attorney, Agent, or Firm*—C. A. Whealy

[57] ABSTRACT

A distinct cultivar of Kalanchoe plant named 'Juliana', characterized by its bright red flower color; large flowers; dark green leaves; and early flowering.

3 Drawing Sheets

The present invention relates to a new and distinct cultivar of Kalanchoe plant, botanically known as *Kalanchoe blossfeldiana*, and hereinafter referred to by the cultivar name 'Juliana'.

The new cultivar is a product of a planned breeding program conducted by the inventor in Hinnerup, Denmark. The objective of the breeding program was to create a new Kalanchoe cultivar having large bright red flowers, dark green leaves and a short production period.

The new cultivar originated from a cross made by the inventor of a proprietary Kalanchoe selection number KJ 9135-066 as the male or pollen parent with a prorietary Kalanchoe selection number KJ 9135-060 as the female or seed parent.

The cultivar 'Juliana' was discoveed and selected by the inventor as a flowering plant within the progeny of the stated cross in a controlled environment in Hinnerup, Denmark. Asexual reproduction of the new cultivar by terminal cuttings taken at Hinnerup, Denmark, has shown that the unique features of this new Kalanchoe are stable and reproduced true to type in successive generations.

The cultivar 'Juliana' has not been observed under all possible environmental conditions. The phenotype may vary somewhat with variations in environment such as temperature, daylength and light intensity, without, however, any variance in genotype.

The following observations, measurements and comparisons describe plants grown in Hinnerup, Denmark, under commercial practice in a glass-covered greenhouse.

The following traits have been repeatedly observed and are determined to be in the unique characteristics of 'Juliana'. These characteristics in combination distinguish 'Juliana' as a new and distinct cultivar:

1. Bright red flower color.
2. Large flowers.
3. Dark green leaves.
4. Early flowering.

The accompanying colored photographs illustrates the overall appearance of the new cultivar, showing the colors as true as it is reasonably possible to obtain in colored reproduction of this type. The photographs were taken under diffuse natural light conditions on an overcast day with electronic flash at approximately noon in Hinnerup, Denmark.

The first photograph comprises a side perspective view of a typical potted plant of 'Juliana'.

The second photograph comprises a top perspective view of a typical potted plant of 'Juliana' showing the flowers.

The third photograph comprises from left to right: a top perspective view of a typical cyme; a side perspective view of a typical cyme; an individual flower; adaxial (above) and abaxial (below) surfaces of immature leaves; and adaxial (above) and abaxial (below) surfaces of fully mature leaves.

Flower and foliage colors in the photographs may appear different from the actual colors due to light reflectance.

In the following description, color references are made to The Royal Horticultural Society Colour Chart except where general terms of ordinary dictionary significance are used.

Botanical classification: *Kalanchoe blossfeldiana* cultivar 'Juliana'.

Parentage:

*Male or pollen parent.*—*Kalanchoe blossfeldiana* proprietary selection KJ 9135-066.

*Female or seed parent.*—*Kalanchoe blossfeldiana* proprietary selection KJ 9135-060.

Propagation:

*Type cutting.*—Terminal cuttings.

*Time to initiate roots.*—About twelve days.

*Rooting habit.*—Numerous, fine, fibrous, and well-branched.

Plant description:

*Form.*—Compact and upright; plant shape is columnar or an inverted triangle with a rounded apex. Actual plant shape will depend on whether or not plants are pinched (vegetative terminals removed). Appropriate for 9 to 10-cm containers with one cutting per container and also for 12-cm containers with three cutting per container.

*Branching habit.*—Freely brancing, generally shoots formed at every node.

*Plant height at flowering.*—About 24 cm.

*Plant diameter at flowering.*—About 20 cm.

*Vigor.*—Moderately vigorous and moderated growth rate.

*Foliage description.*—Leaves simple, opposite, generally symmetrical. Size: Leaf size is reduced after floral induction. Vegetative plants: Length: About 11.5 cm. Width: About 9 cm. Reproductive plants: Length: About 7.5 cm. Width: About 4.5 cm. Shape: Ovate to oval. Apex: Obtuse. Base: Obtuse. Margin:

Crenate. Texture: Leathery, glabrous, and succulent. Color: Young foliage upper side: 147A. Young foliage under side: 147A. Mature foliage upper side: 147A. Mature foliage under side: 147B.

Flower description:

*Flower type and habit.*—Single flowers arranged in compound dichasial cymes. The main inflorescence are branched into one primary and 2 to 4 minor cymes during development. Freely flowering. Flowers persistent.

*Natural flowering season.*—Autumn/winter/early spring; flower initiation and development can be induced under short day/long night conditions.

*Inflorescences borne.*—Above foliage, arising from leaf axils.

*Time to flower.*—In the summer with 20° C. growing temperatures, about 9 weeks of short day/long night conditions are required to produce flowering plants. During the winter with supplemental lighting and 20° C. growing temperatures, about 10 weeks of short day/long night conditions are required to produce flowering plants. Time to flower is primarily dependent upon temperature and light intensity.

*Flower opening.*—First flower open is the terminal flower at the main axis and is followed by the opening of the terminal flowers of the side branches of the inflorescence. About one week after the first flower has opened, 50% of the remaining flowers are open.

*Flower diameter.*—About 2.1 cm.

*Quantity.*—On unpinched plants, at least 200 flowers per plant.

*Flower buds.*—Shape: Oblong becoming tubular/ovoid with development. Size: Length: About 1.5 cm. Width: About 3 mm. Color: 46A.

*Petals*—Quantity: Four fused at base to form bell-shaped corolla. Length: About 1 cm. Shape: Obovate. Apex: Cuspidate. Margin: Entire. Texture: Glabrous, smooth and satiny. Color: When opening: 45A. Mature, upper side: 45B/45C. Mature, under side: 66B.

*Reproductive organs.*—Stamens: Stamen number: Eight. Anther shape: Slightly oblong. Filament color: Yellow green. Pollen color: Yellow. Pistils: Pistil number: Four. Stigma shape: Round. Style color: Green. Ovaries: Hypogenous and four-celled. Ovary size: 5 by 1 mm. Ovary color: Light green.

Disease resistance: No known Kalanchoe diseases observed to date under commercial practice.

Seed production: Seed production has not been observed.

It is claimed:

1. A new and distinct cultivar of Kalanchoe plant named 'Juliana', as illustrated and described.

* * * * *

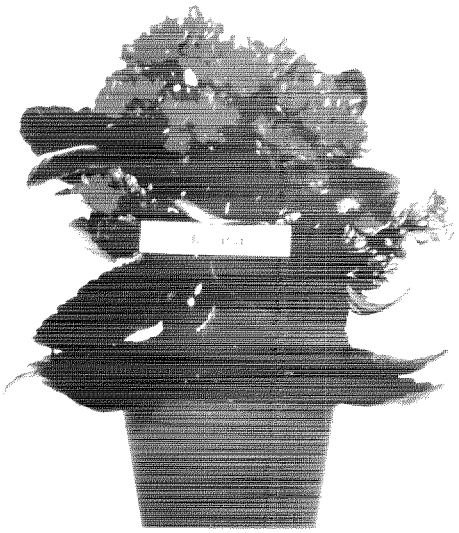

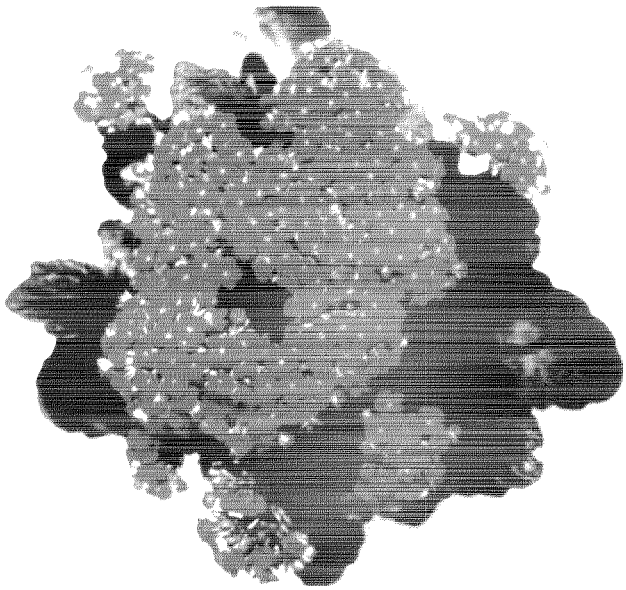

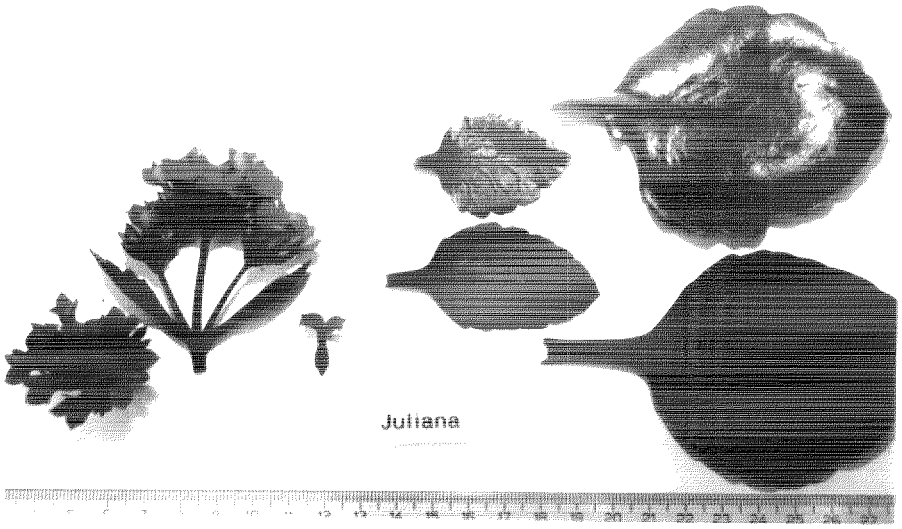
Juliana